United States Patent [19]
Hill

[11] Patent Number: 5,583,897
[45] Date of Patent: Dec. 10, 1996

[54] METHOD FOR DETERMINING NUCLEAR REACTOR FUEL PELLET DENSITY USING GAS DISPLACEMENT

[75] Inventor: Donald J. Hill, Richland, Wash.

[73] Assignee: Siemens Power Corporation, Richland, Wash.

[21] Appl. No.: 365,276

[22] Filed: Dec. 28, 1994

[51] Int. Cl.⁶ .............................. G21C 17/00; G01N 9/26
[52] U.S. Cl. ............................................. 376/245; 73/149
[58] Field of Search ...................... 376/245, 261; 73/32 R, 37, 149, 433, 434

[56] References Cited

U.S. PATENT DOCUMENTS

| 4,193,502 | 3/1980 | Marmo | 376/245 |
| 5,074,146 | 12/1991 | Orr et al. | 73/149 |

Primary Examiner—Daniel D. Wasil
Attorney, Agent, or Firm—Ira Lee Zebrak, Esq.

[57] ABSTRACT

A method for determining the density of nuclear fuel pellet using gas displacement and isothermal gas expansion.

2 Claims, 2 Drawing Sheets

METHOD FOR DETERMINING NUCLEAR REACTOR FUEL PELLET DENSITY USING GAS DISPLACEMENT

INTRODUCTION

1. Field of the Invention

The present invention relates to a method of determining the density of nuclear fuel pellets for nuclear fuel to be used in reactors, and more particularly to a method of determining the density of fuel pellets using gas displacement.

2. Background

During the manufacture of nuclear fuel, the density of nuclear fuel pellets, regardless of physical geometry, is a critical parameter affecting nuclear fuel performance and which is influenced by a variety of processing variables. As a result, density measurements must be taken at key points in the production process of both green (i.e. unsintered) and sintered fuel pellets to monitor and control the fabrication parameters. Traditionally, these density measurements require weighing of sample pellets followed by determination of the pellet volume by methods such as mensuration methods (i.e. measurement of pellet dimensional attributes) or liquid immersion/displacement methods. These methods have the disadvantages of being time-consuming and subject to error due for example to surface anomalies in the case of mensuration density testing.

OBJECT OF THE INVENTION

It is an object of the invention to provide a method of determining the density of nuclear fuel pellet which is faster, simpler and more accurate than those methods which utilize either mensuration methods or liquid immersion/displacement methods.

SUMMARY OF THE INVENTION

A process for determining the density of a sample nuclear fuel pellet using gas displacement comprising the steps of: determining the volume of a valve manifold volume without a sample nuclear fuel pellet by providing a first amount of gas into a calibrated reference volume having a predetermined volume and measuring the pressure of the amount of gas in the calibrated reference volume; allowing the first amount of gas in the calibrated reference volume to expand isothermally from the calibrated reference volume into the valve manifold volume without a sample nuclear fuel pellet and measuring the pressure of the first amount of gas in the calibrated reference volume and the valve manifold volume; determining the volume of the valve manifold volume within which a sample nuclear fuel pellet is placed by placing a sample nuclear fuel pellet whose density is to be determined within the valve manifold volume; providing a second amount of gas into the calibrated reference volume and measuring the pressure of the second amount of gas in the calibrated reference volume; allowing the second amount of gas to expand isothermally from the calibrated reference volume into the valve manifold volume within which is placed a sample nuclear fuel pellet and measuring the pressure of the second amount of gas in the calibrated reference volume and the valve manifold volume, where the difference between the volume of the valve manifold without the sample nuclear fuel pellet and the volume of the valve manifold with the sample is the volume of the sample; and measuring the weight of the sample nuclear fuel pellet to determine its mass.

DETAILED DESCRIPTION

The present invention is directed to a method to quickly and accurately determine the density of objects, and more particularly nuclear fuel pellets used in the manufacture and fabrication of nuclear fuel rods for reactors, using gas displacement measurements. Although the following detailed description refers to nuclear fuel pellets as the test or sample object, the density of virtually any material can be determined by the present invention. According to the invention, a dry non-reactive gas is allowed to expand from a measured pressure in a calibrated volume into a manifold which includes a sample test chamber. The resulting pressure, with and without test samples present, is measured using a high precision pressure transducer. The pressure readings allow calculation of the displacement volume of the test object(s), which taken with the measured mass of the sample provides the density. The method has the advantage of being less error prone than mensuration methods, is faster and simpler than the painstaking water immersion density testing, and may be automated in terms of measurements, data processing and pellet handling. Added precision may be obtained by measuring a composite sample of pellets at one time, whereas in mensuration tests a composite sample cannot be utilized, and water immersion density tests for composite samples become even more painstaking.

Figure 1:
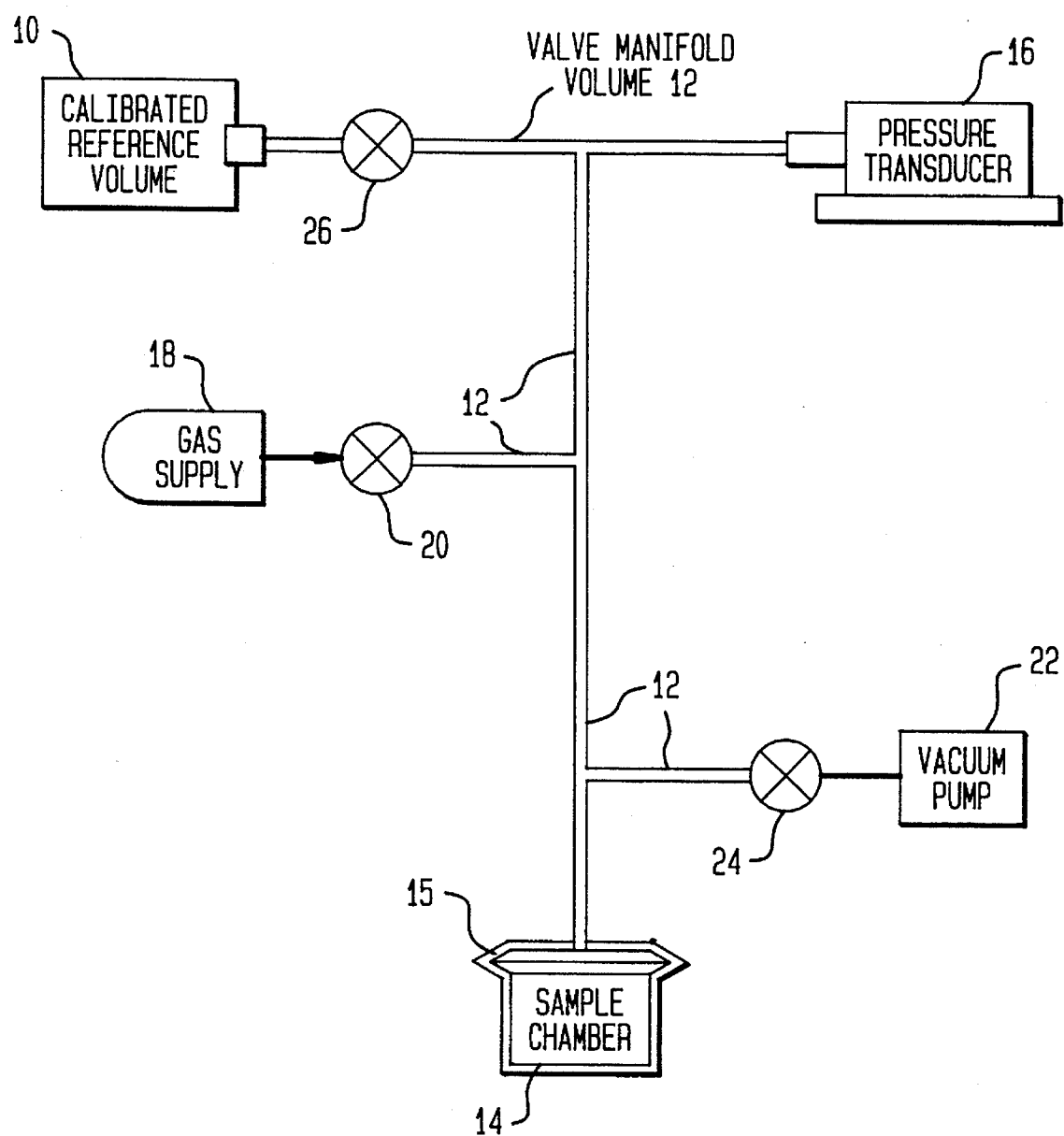
FIG. 1 is a system schematic of a nuclear fuel pellet density measurement system of a first embodiment of the present invention.

The gas displacement nuclear reactor fuel pellet density measurement method determines sample pellet volume based on isothermal gas expansion. Referring to FIG. 1, the gas displacement nuclear reactor fuel pellet system comprises a calibrated reference volume 10 of volume $V_c$, valve manifold 12 (of volume $V_m$) which includes piping and a removable sample chamber 14 in which test specimens may be placed and vacuum pressure seal/vent 15, and a high precision/high accuracy pressure transducer 16. Gas, either an inert gas, air, nitrogen or virtually any other dry non-reactive gas is introduced from a pressurized source 18 by means of a valve 20, and which is evacuated via a vacuum pump 22 by means of a valve 24. Between calibrated reference volume 10 and valve manifold 12 is valve 26 which functions when closed to isolate the calibrated reference volume 10 and the valve manifold volume 12 from one another.

The process for determining the sample fuel pellet density by using gas displacement comprises the steps of first determining the valve manifold volume without a pellet sample, and second determining the valve manifold volume with a sample.

Although the valve manifold volume can be determined by several methods including water calibration in which it is filled with water and weighed both before and after filling, it is a preferred embodiment of the present invention to determine the valve manifold volume utilizing the system shown in FIG. 1 employing isothermal gas expansion as follows:

(a) evacuating valve manifold volume 12 and calibrated reference volume 10 by opening calibrated reference volume isolation valve 26 and vacuum pump valve 24, activating evacuation pump 22, and closing vacuum pump valve 24;

(b) pressurizing the valve manifold volume 12 and calibrated reference volume 10 with gas from gas supply 18 to an initial pressure $P_i$ which is measured by pressure transducer 16 by opening and closing gas supply valve 20;

(c) isolating calibrated reference volume 10 from the valve manifold volume by closing calibrated reference volume isolation valve 26;

(d) evacuating valve manifold volume 12 by opening vacuum pump valve 24, activating evacuation pump 22, and closing vacuum pump valve 24;

(e) expanding gas in calibrated reference volume 10 into the valve manifold volume 12 by opening calibrated reference volume isolation valve 26; and (f) measuring the final pressure $P_f$ of the calibrated reference volume 10 and the valve manifold volume 12 by pressure transducer 16.

The volume of valve manifold volume 12 is then determined based on isothermal gas expansion, or Boyle's Law where $P_1V_1=P_2V_2$ where the subscripts 1 and 2 refer to the initial and final states, and the temperature is kept constant. Applying Boyle's Law to the above described process:

$$P_iV_c=P_f(V_c+V_m) \qquad \text{(Equation 1)}$$

where $P_i$=measured initial pressure of the calibrated reference volume 10 (See (b) above), $V_c$=known volume of calibrated reference volume 10;

$P_f$=measured final pressure of the calibrated reference volume 10 and valve manifold volume 12; and $V_m$=volume of valve manifold volume 12.

Rearranging Equation 1 yields $$V_m = \frac{V_c(P_i - P_f)}{P_f} \qquad \text{(Equation 2)}$$

Since $V_c$ is known and both $P_i$ and $P_f$ have been measured, $V_m$ is thereby determined.

Next, a sample fuel pellet (or pellets) is placed within sample chamber 14 and steps (a) through (f) are repeated to find the volume of the valve manifold with the sample present. The volume of the valve manifold with the sample present is $V'_m$ and is similarly determined by:

$$V_m' = \frac{V_c(P_i' - P_f')}{P_f'} \qquad \text{(Equation 3)}$$

where $V'_m$=volume of valve manifold volume 12 with the sample in the sample chamber;

$V_c$=volume of calibrated reference volume 10;

$p'_i$=measured initial pressure of calibrated reference volume 10; and $p'_f$=measured final pressure of calibrated reference volume 10 and valve manifold volume 12 with the sample in the sample chamber.

Since $V_c$ is known and both $P'_i$ and $P'_f$ have been measured, $V'_m$ is thereby determined by Equation 3.

The density $\rho_s$ of the sample(s) is defined as:

$$\rho_s = \frac{M_s}{V_s} \qquad \text{(Equation 4)}$$

where $M_s$=mass of the sample which is determined by weighing; and $V_s$=volume of the sample.

Since the volume of the sample $V_s$ is the difference between the volume of the valve manifold without the sample $V_m$ and the volume of the manifold with the sample $V'_m$, $V_s$ is represented by:

$$V_s = V_m - V'_m \qquad \text{(Equation 5)}$$

Then, substituting Equation 5 into Equation 4 yields:

$$\rho_s = \frac{M_s}{V_m - V'_m} \qquad \text{(Equation 6)}$$

Since $M_s$, $V_m$ and $V'_m$ have been measured the density of the sample $\rho_s$ is thereby determined by Equation 6.

Figure 2:
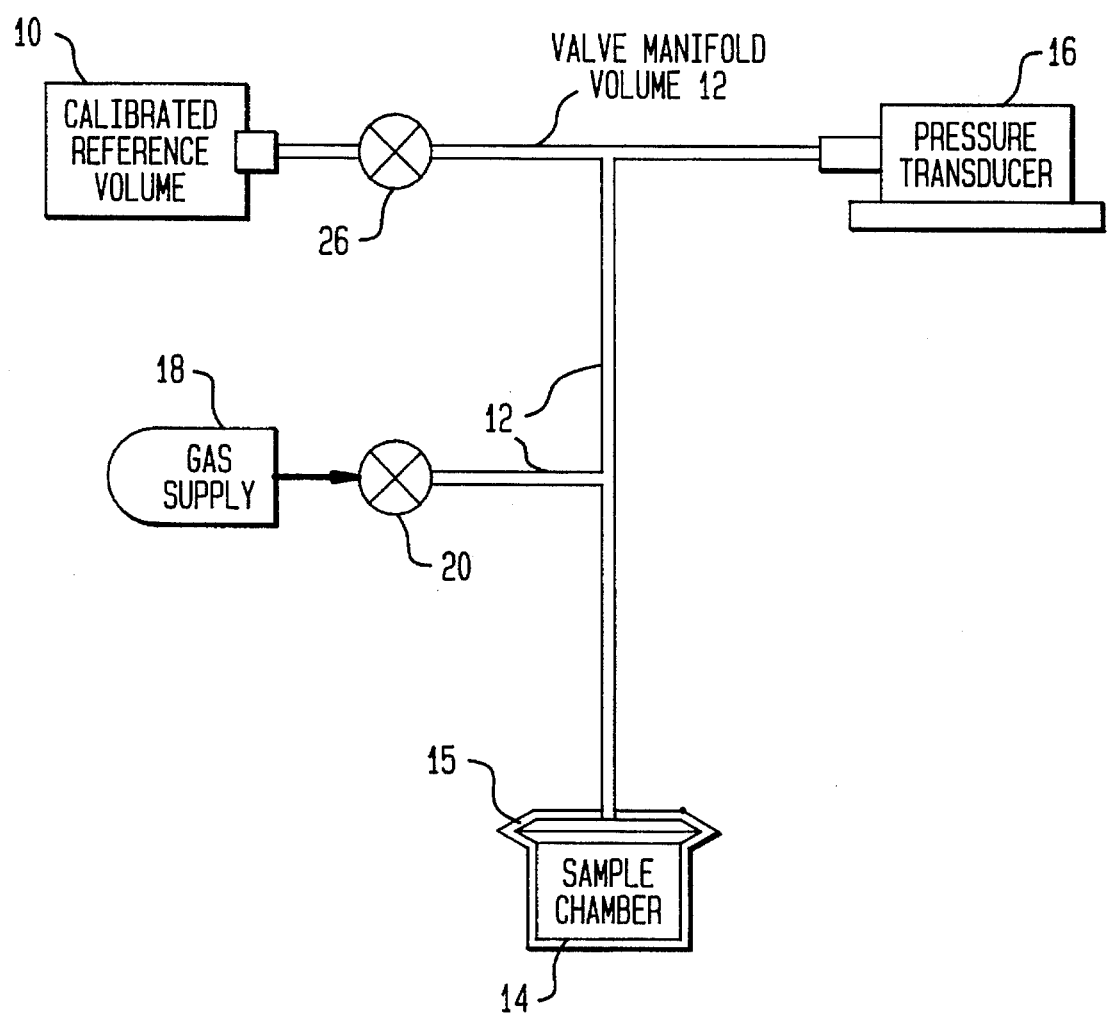
FIG. 2 is a system schematic of a nuclear fuel pellet density measurement system of a second embodiment of the present invention.

In an alternative embodiment in which the gas displacement nuclear reactor fuel pellet density system is chosen to be operated above atmospheric pressures, the vacuum pump 22 and valve 24 as well as associated portion of the valve manifold is omitted as shown in FIG. 2. In this embodiment, the volume of the valve manifold without a sample is determined by the following:

(A) pressurizing the valve manifold volume 12 and calibrated reference volume 10 with gas from gas supply 18 to an initial pressure $P_i$ which is measured by pressure transducer 16 by opening calibrated reference volume isolation valve 26 and opening gas supply valve 20 and then closing supply valve 20;

(B) isolating calibration reference volume 10 by closing calibrated reference volume isolation valve 26;

(C) venting valve manifold volume 12 through the vent 15 on sample chamber 14 and closing vent;

(D) expanding gas in calibrated reference volume 10 into the valve manifold volume 12 by opening calibrated reference volume isolation valve 26; and (E) measuring the final pressure $P_f$ of the calibrated reference volume 10 and the valve manifold volume 12 by pressure transducer 16.

The volume of the calibrated reference volume without a sample $V_m$ is then determined by Equation 2. A sample pellet (or pellets)

TABLE 1

Gas Immersion Density Tests

| Test | Pressure (atm) | Measurements | Accuracy (1) | Precision (RSD) |
|---|---|---|---|---|
| 1 | 2⅓ | 3 | 100.95% | 0.02% |
| 2 | 2⅔ | 3 | 99.71% | 0.02% |
| 3 | 2⅔ | 3 | 100.69% | 0.0003% |
| 4 | 2⅔ | 3 | 99.36% | 0.02% |
| 5 | 1½ | 3 | 89.75% | 0.04% |
| 6 | 2⅔ | 3 | 101.53% | 0.01% |
|  |  |  | X̄98.665 | 0.018% |
| (Rejecting Test 5: |  |  | X̄100.448 | 0.014% |
| MDR[2] 3 Tests, 3 Each |  |  |  | 0.07% |
| Water Immersion[3] (Reference Method) |  |  | -(100)- | 0.05% |

[1] Results relative to Laboratory water immersion density tests.
[2] Micrometer Dimensional Readings and sample weighing to compute density.
[3] Precision based on triplicate tests.

is placed within sample chamber 14 and steps A through E are repeated to determine the volume of the valve manifold with a sample $V'_m$ which is then determined by Equation 3. The sample is then weighed and its mass determined, and the density of the sample is found by Equation 6.

Laboratory tests using the method of the present invention have been conducted. Summary data of these tests are provided in Table 1. These tests were performed using metal test pellet(s) measured in triplicate with a non-optimized gas pressure valve manifold. Tests 1, 2, and 3 employed a single test specimen, run at initial pressure from 2 ⅓ to 2 ⅔ atmospheres; tests 4, 5, and 6 were run with multiple specimens (larger composite volume) at pressures as indicated. With the exception of one test conducted at low pressure, relative measurement accuracy of 99.36% to 101.53% were obtained at various test conditions. A typical mensuration density system provides an accuracy of approximately ±0.2%. In terms of precision, the relative standard deviation (RSD) of these tests ranged from <0.04% to 0.021% while the mensuration density system under similar conditions tested at 0.07%. These tests and sensitivity calculations indicate that an optimized measurement system with reduced manifold volume will further provide even greater accuracy. Testing and sensitivity calculations were performed and indicate that the highest accuracy and precision will be obtained when $V_m$ is small relative to sample volume, and $V_c$ is approximately equal to $V_m$. Added precision may be obtained by measuring a composite sample of pellets at one time.

The speed, simplicity, and accuracy of the present invention renders it a significant improvement over density measurement methods of the prior art. The added advantage of its use for green pellet density measurements as well as density of unground pellets enables it to be utilized in-process (real time) variable measurements in lieu of final acceptance sampling on a lot basis.

While the foregoing description and drawings represent the preferred embodiments of the present invention, it will be apparent to those skilled in the art that various changes and modifications may be made therein without departing from the true spirit and scope of the present invention.

I claim:

1. A process for determining the density of a sample nuclear fuel pellet using gas displacement comprising the steps of:

determining the volume of a valve manifold volume without a sample nuclear fuel pellet by;

providing a first amount of gas into a calibrated reference volume having a predetermined volume and measuring the pressure of the amount of gas in the calibrated reference volume;

evacuating the valve manifold volume;

allowing the first amount of gas in the calibrated reference volume to expand isothermally from the calibrated reference volume into the valve manifold volume without a sample nuclear fuel pellet and measuring the pressure of the first amount of gas in the calibrated reference volume and the valve manifold volume;

determining the volume of the valve manifold volume within which a sample nuclear fuel pellet is placed by;

placing a sample nuclear fuel pellet whose density is to be determined within the valve manifold volume;

providing a second amount of gas into the calibrated reference volume and measuring the pressure of the second amount of gas in the calibrated reference volume;

evacuating the valve manifold volume;

allowing the second amount of gas to expand isothermally from the calibrated reference volume into the valve manifold volume within which is placed a sample nuclear fuel pellet and measuring the pressure of the second amount of gas in the calibrated reference volume and the valve manifold volume, where the difference between the volume of the valve manifold without the sample nuclear fuel pellet and the volume of the valve manifold with the sample is the volume of the sample; and measuring the weight of the sample nuclear fuel pellet to determine its mass.

2. A process for determining the density of a sample nuclear fuel pellet using gas displacement comprising the steps of:

determining the volume of a valve manifold volume without a sample nuclear fuel pellet by;

evacuating a valve manifold volume and a calibrated reference volume having a predetermined volume and which is interconnected to the valve manifold volume;

pressurizing the valve manifold volume and the calibrated reference volume with a first amount of gas from a gas supply to an initial pressure $P_i$ and measuring the initial pressure;

isolating the calibrated reference volume from the valve manifold volume;

evacuating the valve manifold volume;

expanding the first amount of gas in the calibrated reference volume isothermally into the valve manifold volume; and measuring the final pressure $P_f$ of the first amount of gas in the calibrated reference volume and the valve manifold volume;

determining the volume of the valve manifold volume within which is placed a sample nuclear fuel pellet by;

placing a sample nuclear fuel pellet whose density is to be determined within the valve manifold volume;

evacuating the valve manifold volume and the calibrated reference volume;

pressurizing the valve manifold volume and the calibrated reference volume with a second amount of gas from a gas supply to an initial pressure $P_i$ and measuring the initial pressure;

isolating the calibrated reference volume from the valve manifold;

evacuating the valve manifold volume;

expanding the second amount of gas in the calibrated reference volume isothermally into the valve manifold volume; and measuring the final pressure $P_f$ of the second amount of gas in the calibrated reference volume and the valve manifold volume;

where the difference between the volume of the valve manifold without the sample nuclear fuel pellet and the volume of the valve manifold with the sample is the volume of the sample; and measuring the weight of the sample nuclear fuel pellet to determine its mass.

* * * * *